(12) United States Patent
Ford

(10) Patent No.: US 8,653,090 B2
(45) Date of Patent: Feb. 18, 2014

(54) COMPOSITIONS AND METHODS FOR TREATMENT OF THE SIDE-EFFECTS ASSOCIATED WITH ADMINISTRATION OF CANCER CHEMOTHERAPEUTIC AGENTS

(75) Inventor: John P. Ford, Unadilla, NY (US)

(73) Assignee: Asymmetric Therapeutics, LLC, Unadilla, NY (US)

( * ) Notice: Subject to any disclaimer, the term of this patent is extended or adjusted under 35 U.S.C. 154(b) by 0 days.

(21) Appl. No.: 13/446,328

(22) Filed: Apr. 13, 2012

(65) Prior Publication Data

US 2012/0244211 A1 Sep. 27, 2012

Related U.S. Application Data

(63) Continuation-in-part of application No. 12/381,474, filed on Mar. 12, 2009, now abandoned.

(60) Provisional application No. 61/069,031, filed on Mar. 12, 2008.

(51) Int. Cl.
*A01N 43/90* (2006.01)
*A61K 31/52* (2006.01)
*C07D 473/00* (2006.01)
*A61K 9/127* (2006.01)

(52) U.S. Cl.
USPC .................. 514/263.4; 544/277; 424/450

(58) Field of Classification Search
None
See application file for complete search history.

(56) References Cited

U.S. PATENT DOCUMENTS

| | | | |
|---|---|---|---|
| 6,723,737 B1 * | 4/2004 | Rapaport | 514/310 |
| 6,995,165 B2 * | 2/2006 | Ford | 514/274 |
| 8,034,823 B2 * | 10/2011 | Karmali | 514/274 |
| 2009/0131344 A1 | 5/2009 | Karmali | |
| 2012/0244211 A1 * | 9/2012 | Ford | 424/450 |

OTHER PUBLICATIONS

Verma, et al. (2000) "Osmotically Controlled Oral Drug Delivery", Drug Development and Industrial Pharmacy, 26(7): 695-708.*
Fox, et al. (1981) "Allopurinol Modulation of Fluorouracil Toxicity", Cancer Chemotherapy and Pharmacology, 5: 151-55.*
Bartlett, "Erythrocyte Metabolism", pp. 10-13 in Adenine and Red Cell Storage, The Human Red Cell in Vitro, Greenwald et al., ed., New York: Grune and Stratton, 1974.
Bührdel et al., "Adenine Therapy in Lesch-Nyhan Syndrome", Acta Paediatrica Hungarica, vol. 26, pp. 327-333, 1985.
"Care During Chemotherapy", available at http://web.archive.org/web/20080310230202/http://www.chemocare.com/whatis/types_of_chemotherapy.asp, 3 pages, Mar. 10, 2008.
Hoff, "The tegafur-based dihydropyrimidine dehydrogenase inhibitory fluoropyrimidines, UFT/leucovorin (ORZWL) and S-1: a review of their clinical development and therapeutic potential", Investigational New Drugs, vol. 18, pp. 331-342, 2000.
Ichikawa et al., "Orotate Phosphoribosyltransferase Gene Polymorphism Predicts Toxicity in Patients Treated with Bolus 5-Fluorouracil Regimen", Clinical Cancer Research, vol. 12, pp. 3928-3933, 2006.
Plunkett et al., "Gemcitabine: Metabolism, Mechanisms of Action and Self-potentiation", Seminars in Oncology, vol. 4, pp. 3-10, 1995, abstract only.
Robinson et al., "Effects of Orotic Acid Ingestion on Urinary and Blood Parameters in Humans", Nutrition Research, vol. 3, pp. 407-415, 1983.
Salati et al., "Absorption and Metabolism of Adenine, Adenosine-5'-Monophosphate, Adenosine and Hypoxanthine by the Isolated Vascularly Perfused Rat Small Intestine", Journal of Nutrition, vol. 114, pp. 753-760, 1984.
Torchilin, "Recent Advances with Liposomes as Pharmaceutical Carriers", Nature Reviews: Drug Discovery, vol. 4, pp. 145-160, 2005.
Van Acker et al., "Complete Deficiency of Adenine Phosphoribosyltransferase", The New England Journal of Medicine, vol. 297, pp. 127-132, 1977.
Verma, et al., "Osmotically Controlled Oral Drug Delivery", Drug Development and Industrial Pharmacy, vol. 26, pp. 695-708, 2000.
Lian et al., "Trends and Developments in Loipsome Drug Delivery Systems", Journal of Pharmaceutical Sciences, vol. 90, pp. 667-680, 2001.
International Search Report and Written Opinion for PCT/US2013/036326, dated Jul. 29, 2013, 12 pages.

* cited by examiner

*Primary Examiner* — Robert M Kelly
(74) *Attorney, Agent, or Firm* — Brown & Michaels, PC

(57) ABSTRACT

A composition and method for the treatment of the side-effects associated with the administration of cancer chemotherapeutic agents involves the oral ingestion of a slow release capsule containing adenine and orotate. The administration of a protein pump inhibitor decreases systemic absorption of orotate and the administration of allopurinol decreases the formation of 2,8-dihydroxy adenine from adenine. In an alternative embodiment, cationic liposomes contain purine/pyrimidine precursors. The cationic liposomes bind to the cells lining the mucosa of the intestinal tract and then the contents of the cationic liposome are then taken up in the interior of the cells to prevent the metabolism of the cancer treatment drug 5-FU into a toxic species.

25 Claims, 3 Drawing Sheets

A: 5FU (0.01 mM) O (0 mM) A (0 mM)
B: 5FU (0.01 mM) O (2.5 mM) A (0.62 mM)
C: 5FU (0.01 mM) O (2.5 mM) A (1.2 mM)
D: 5FU (0.01 mM) O (2.5 mM) A (2.5 mM)

A: 5FU (0.01 mM) O (0 mM) A (0 mM)
E: 5FU (0.01 mM) O (1.25 mM) A (0 mM)
F: 5FU (0.01 mM) O (1.25 mM) A (0.0125 mM)
G: 5FU (0.01 mM) O (1.25 mM) A (0.125 mM)
H: 5FU (0.01 mM) O (1.25 mM) A (1.25 mM)

A: 5FU (0.01 mM) O (0 mM) A (0 mM) I (0 mM)
D: 5FU (0.01 mM) O (2.5 mM) A (2.5 mM) I (0 mM)
I: 5FU (0.01 mM) O (2.5 mM) A (0 mM) I (2.5 mM)

A: 5FU (0.01 mM) O (0 mM) A (0 mM) U (0 mM)
D: 5FU (0.01 mM) O (2.5 mM) A (2.5 mM) U (0 mM)
J: 5FU (0.01 mM) O (2.5 mM) A (2.5 mM) U (1.25 mM)
K: 5FU (0.01 mM) O (2.5 mM) A (2.5 mM) U (2.5 mM)

COMPOSITIONS AND METHODS FOR TREATMENT OF THE SIDE-EFFECTS ASSOCIATED WITH ADMINISTRATION OF CANCER CHEMOTHERAPEUTIC AGENTS

REFERENCE TO RELATED APPLICATIONS

This is a continuation-in-part patent application of application Ser. No. 12/381,474, filed Mar. 12, 2009, entitled "COMPOSITION AND METHOD FOR TREATMENT OF THE SIDE-EFFECTS ASSOCIATED WITH ADMINISTRATION OF CANCER CHEMOTHERAPEUTIC AGENTS", now abandoned, which claims one or more inventions which were disclosed in Provisional Application No. 61/069,031, filed Mar. 12, 2008, entitled "COMPOSITION AND METHOD FOR TREATMENT OF THE SIDE-EFFECTS ASSOCIATED WITH ADMINISTRATION OF CANCER CHEMOTHERAPEUTIC AGENTS". The benefit under 35 USC §119(e) of the United States provisional application is hereby claimed, and the aforementioned applications are hereby incorporated herein by reference.

BACKGROUND OF THE INVENTION

1. Field of the Invention

The invention pertains to the field of ameliorating the effect of drugs on the human body. More particularly, the invention pertains to a composition and a method for treatment of the side-effects associated with the administration of cancer chemotherapeutic agents, specifically 5-fluorouracil (5-FU).

2. Description of Related Art

Human beings who develop cancer are often treated with chemotherapeutic drugs. Cancer chemotherapeutic drugs, while effective at destroying a cancerous tumor, may also cause damage to normal tissues of the body. The normal tissues of the body most often affected by the side-effects of a cancer chemotherapeutic drug include the lining of the mouth, the lining of the intestine, and the hair. Symptoms associated with the deleterious effects of chemotherapeutic cancer drugs include hair loss, nausea, and vomiting. Occasionally, the side-effects associated with the administration of cancer chemotherapeutic drugs can be debilitating and result in interruptions of the cancer chemotherapeutic drug treatment regimen.

Various attempts have been made to lessen or to eliminate the symptoms associated with the administration of 5-fluorouracil (5-FU). One approach to mitigate the toxicity of 5-FU is to combine a 5-FU precursor drug with other agents such as oral oxonic acid and 5-chloro-2,4-dihydroxypyridine in the case of S-1. These agents have their own toxicities, including gastrointestinal (GI) toxicity (see, for example, Hoff, "The tegafur-based dihydropyrimidine dehydrogenase inhibitory fluoropyrimidines, UFT/leucovorin (ORZWL) and S-1: a review of their clinical development and therapeutic potential", *Investigational New Drugs*, Vol. 18, pp. 331-342, 2000). Other drugs, such as steroids, have been administered to patients to alleviate the suffering associated with the side-effects of cancer treatment using chemotherapy. The success associated with the use of these other drugs to alleviate suffering has not been successful, and as a consequence, the "treatment" is to lower the dose of 5-FU.

Another problem associated with these other drugs is that drugs such as steroids and other drugs used to alleviate the side-effects of cancer drugs may be toxic to other tissues. Such tissue toxicity produces additional unwanted side-effects.

A third problem associated with drugs administered to alleviate the side-effects of cancer therapy is that the drug used to alleviate the side-effects caused by the cancer drug may interfere with the activity of the cancer drug, resulting in diminished effectiveness for destroying the targeted cancerous tumor.

Accordingly, there remains a need in the art for a composition and method for the treatment of the side-effects associated with the administration of 5-FU and 5-FU precursor drugs, such as capecitabine.

SUMMARY OF THE INVENTION

A composition and method for the treatment of the side-effects associated with the administration of cancer chemotherapeutic agents involves the oral ingestion of a slow release capsule containing adenine and orotate. The administration of a protein pump inhibitor decreases systemic absorption of orotate, and the administration of allopurinol decreases the formation of 2,8-dihydroxy adenine from adenine. In an alternative embodiment, cationic liposomes contain purine/pyrimidine precursors. The cationic liposomes bind to the cells lining the mucosa of the intestinal tract and then the contents of the cationic liposome are then taken up in the interior of the cells to prevent the metabolism of the cancer treatment drug 5-FU into a toxic species.

DETAILED DESCRIPTION OF THE INVENTION

Figure 1:
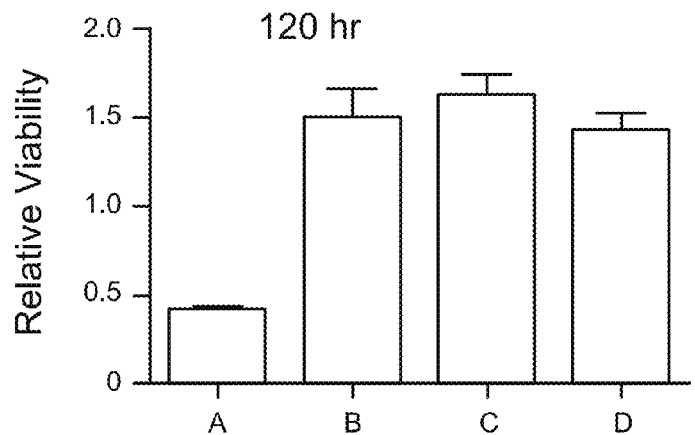
FIG. 1 shows the effect of different levels of adenine in combination with 2.5 mM orotate on the growth of human-derived colon (Caco-2) cells exposed to 5-FU in cell culture.

The approach described herein to alleviate the toxicity of 5-FU to the GI tract and its associated suffering is to deliver the mitigating drug directly to the organ affected by the cancer treatment drug, which causes undesirable organ toxicity, in this case to the GI tract. This asymmetric delivery of toxicity prevention only to the tissue subject to the toxicity can allow a higher dose of anti-cancer medicine to be given to treat the cancer.

Compositions and methods for the treatment of the side-effects associated with administration of cancer chemotherapeutic agents are disclosed herein. A protective formulation is orally administered to the patient. The protective formulation includes at least one natural substrate of at least one enzyme that also metabolizes the cancer therapeutic agent. A substrate of an enzyme that metabolizes the cancer therapeutic agent, as used herein, may be any chemical that binds to the enzyme to a degree such that the rate of reaction between the enzyme and the cancer therapeutic agent decreases and the product of the substrate and the enzyme is a normal cell component.

In a preferred embodiment, a protective formulation for 5-FU includes a mixture of adenine (A) and orotate (O) administered orally at concentrations in the range of 0.0074 mM to 2.5 mM of adenine and 0.0064 mM to 2.5 mM of orotate. Experimental results in cell culture show 150% viability of control for growth in the presence of 0.625 mM adenine and 1.25 mM orotate with growth at 5 days despite the concomitant exposure to 0.01 mM of 5-FU. Exposure to adenine/orotate concentrations in the range of 0.001-0.0125 mM, resulted in no meaningful salvage of 5-FU toxicity administered at the therapeutic dose of 0.01 mM. Importantly, both adenine and orotate are normal enzyme substrates and generate normal anabolites. There is no toxicity from their use together or without the concomitant exposure to 5-FU. Other purine and pyrimidine precursors, such as uracil and inosine do not attenuate, but actually exacerbate, the toxicity of 5-FU to human-derived colon (Caco-2) cells.

The salvage effect is quite specific. Interestingly, the metabolism of skin cells is different from GI cells, and uracil treatment actually reduces the toxicity of 5-FU to skin cells (squamous histology, see below).

Although improved results were obtained when the protective formulation was delivered by liposomes, it was also determined that administration of adenine and orotate in solution could protect cells from 5-FU toxicity.

Because the cells lining the mucosa of the intestinal tract are protected from the toxic effects of 5-FU by the protective formulation, the dosage of 5-FU or its active precursor may be increased so as to more effectively destroy the existing cancerous tumor. Moreover, since 5-FU is not being metabolized in the gastrointestinal tract, more 5-FU is available for destruction of the targeted cancerous tumor. Since the toxic side-effects associated with 5-FU metabolism have been ameliorated by the compositions and methods, normal homeostasis is maintained in the GI tract and patients receiving 5-FU for cancer therapy are more likely to adhere to the treatment regimen recommended by their physician. The combination of increased compliance and increased dosage of 5-FU afforded by the compositions and methods improves the outcome associated with 5-FU cancer treatment therapy.

In a preferred embodiment, adenine and orotate are delivered via an osmotically-controlled oral drug delivery system (see, for example, Verma, et al., "Osmotically Controlled Oral Drug Delivery", *Drug Development and Industrial Pharmacy*, Vol. 26, pp. 695-708, 2000). This system preferably delivers adenine and orotate to all the columnar cells throughout the GI tract.

In an alternative embodiment, the protective formulation includes cationic liposomes containing one or more of various purine/pyrimidine precursors that are administered orally to patients receiving 5-FU for cancer treatment. The cationic liposomes containing the purine/pyrimidine precursors bind to the cells lining the mucosa of the intestinal tract. After binding to the cells lining the mucosa of the intestinal tract, the substrate contents of the cationic liposomes are deposited into the interior of the cells lining the mucosa of the intestinal tract. The liposomally-transfected substrates prevent the metabolism of 5-FU into a toxic species, thereby protecting those cells into which the cationic liposome has been deposited from the toxicity associated with administration of 5-FU. The liposomally-transfected substrates protect the cells lining the mucosa of the intestinal tract from any toxicity associated with the administration of the substrate orotate.

The compositions and methods of treating the side-effects of cancer chemotherapeutic drug administration disclosed herein employ substrates of the enzymes which the human body uses to metabolize the cancer treatment drug.

In preferred embodiments, the substrates of the enzymes are incorporated into slow-release capsules. A particularly well-suited drug delivery format is an osmotically-controlled drug delivery system. A preferred use would be for the device to deliver the purine/pyrimidine precursor drug to the columnar cells throughout the GI tract, which extends from the base of the squamous cell-lined esophagus to the squamous cell-lined anus. The push-pull osmotic pump (PPOP) can provide the optimal zero-order release rate kinetics (see, for example, Verma et al.). The PPOP has been used to deliver drugs such as indomethacin and levodopa. Alternative delivery vehicles include devices such as pH-dependent, enzyme degradation-dependent, and matrix- or polymer-dependent devices.

In other embodiments, the substrates of the enzymes are incorporated into cationic liposomes. Such metabolic by-products and enzyme substrates are incorporated into the cationic liposomes to prevent the damage caused by the cancer drug. Oral administration of the slow-release capsules or cationic liposomes promotes incorporation of the enzyme substrates into the cells lining the mucosa of the intestinal tract to which the cancer drug is toxic. Thereby, the toxic effect of the cancer drug is minimized. These substrates of the enzymes used to metabolize the cancer treatment drug are nontoxic to normal tissues. By administering the substrates of the enzymes which metabolize the cancer chemotherapeutic drug orally, the substrates of the enzymes used to metabolize the cancer treatment drug are delivered only to the cells lining the mucosa of the intestinal tract and do not interfere with the activity of the cancer chemotherapeutic drug on the cancerous tumor to which the cancer chemotherapeutic drug is directed.

The compositions and methods are preferably specifically directed to a composition and method for alleviating the gastrointestinal side-effects of 5-fluorouracil (5-FU). The principle of applying locally an agent to reverse the toxicity of a chemotherapy agent may be applicable to alleviating the side-effects of other cancer chemotherapeutic drugs which cause GI toxicity. The cancer chemotherapeutic agent, 5-FU is one of the first cancer drugs identified and is commonly used in the treatment of cancers of the colon, breast, stomach, and other organs of the body. Among other side effects, the common side-effects of 5-FU administration are nausea and diarrhea because of the toxicity exerted by 5-FU on the cells lining the mucosa of the intestinal tract. The metabolic pathway for 5-FU is widely known.

The chemical 5-FU is inactive against cancerous tumors until it is metabolized by the body to the active species. Anabolism of 5-FU to its active species is accomplished by one of three alternate enzyme systems, which are as follows: 1) uridine phosphorylase (UP), 2) thymidine phosphorylase (TP), and 3) orotate phosphoribosyl transferase (OPT). There is evidence that metabolism of 5-FU by OPT results in the clinically-relevant cell toxicity to the gastrointestinal tract caused by 5-FU (see, for example, Ichikawa et al., "Orotate Phosphoribosyltransferase Gene Polymorphism Predicts Toxicity in Patients Treated with Bolus 5-Fluorouracil Regimen", *Clinical Cancer Research*, Vol. 12, pp. 3928-3933, 2006).

Enzymes such as UP, TP, and OPT can be blocked from acting on the primary substrate (e.g. 5-FU) by saturating the active site of the enzyme with a non-competitive substrate. Saturation of the active site of an enzyme with such a substrate decreases the availability of the enzyme for accepting the alternative substrate (e.g., 5-FU) at the active site of the enzyme, where it is metabolized by the enzyme. If a substance has decreased the active access to the enzyme, clearly this substrate is metabolized less by the enzyme.

Figure 2:
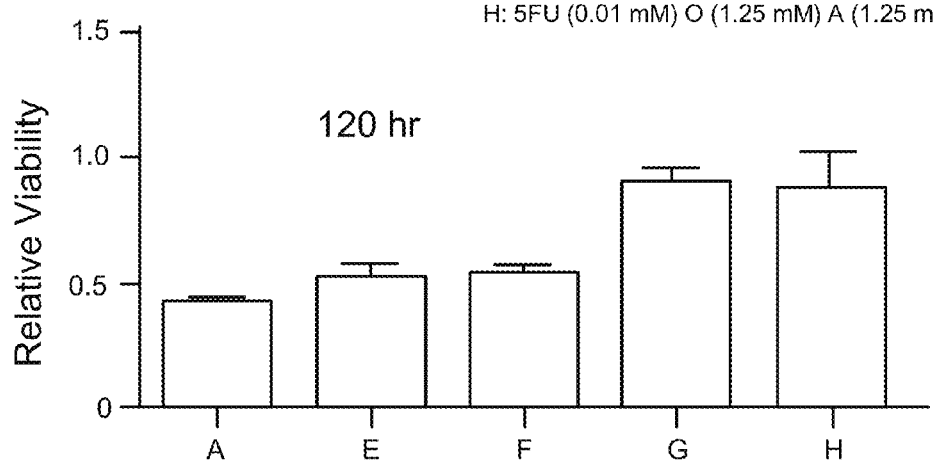
FIG. 2 shows the effect of different levels of adenine in combination with 1.25 mM orotate on the growth of human-derived colon (Caco-2) cells exposed to 5-FU in cell culture.
Figure 3:
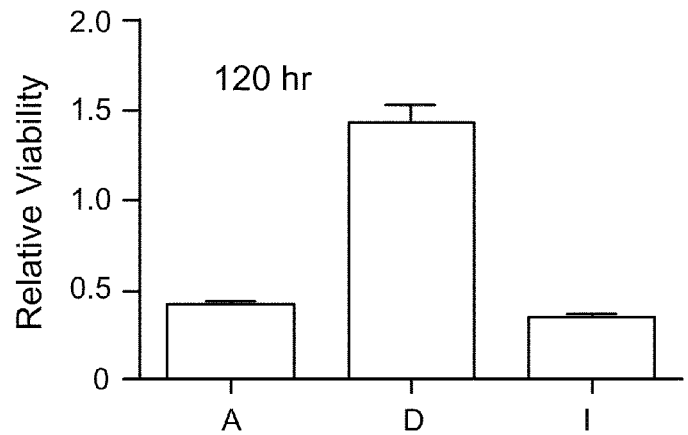
FIG. 3 shows the effect of adenine or inosine in combination with orotate on the growth of human-derived colon (Caco-2) cells exposed to 5-FU in cell culture.
Figure 4:
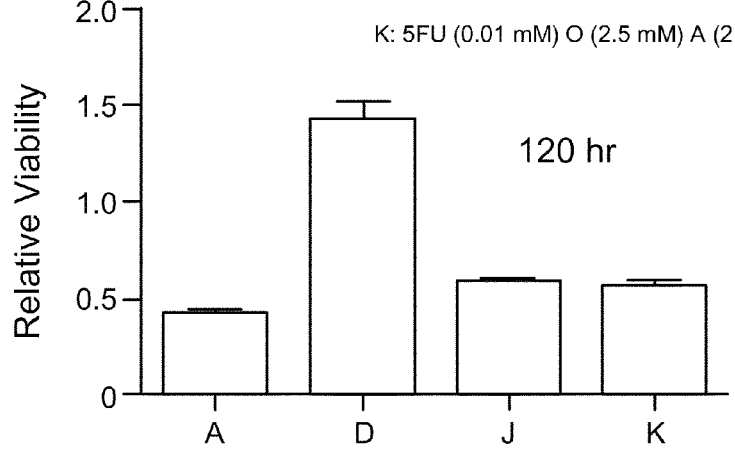
FIG. 4 shows the effect of different levels of uracil in combination with adenine and orotate on the growth of human-derived colon (Caco-2) cells exposed to 5-FU in cell culture.

The efficacy of certain compounds as protective agents when co-administered with 5-FU was tested in cell culture. In one set of experiments, the results of which are shown in FIG. 1, FIG. 2, FIG. 3, and FIG. 4, human-derived colon (Caco-2) cells, commonly used to assess colon cell toxicity, were exposed to the clinically-relevant dose of 0.01 mM 5-FU and different concentrations of orotate (O), adenine (A), uracil (U), and inosine (I) using standard tissue culture methods and incubated at 37° C. The relative viability of the cells was determined after 120 hours. With no orotate, adenine, uracil, or inosine, the relative viability at 120 hours cultured in the presence of 0.01 mM 5-FU was less than 50% that of control cultures incubated without 5-FU present (Result A). With exposure to 0.01 mM 5-FU, 2.5 mM orotate, and adenine in the range of 0.62 mM to 2.5 mM, the relative viability at 120 hours was about 150% as shown in FIG. 1 (Results B, C, and D), indicating that the orotate/adenine combination is able to protect the cells from the 5-FU toxicity. With exposure to 0.01 mM 5-FU, 1.25 mM orotate, and adenine in the range of 0.125 mM to 1.25 mM, the relative viability at 120 hours was about 100% as shown in FIG. 2 (Results G and H), indicating that the orotate/adenine combination is able to protect the cells from the 5-FU toxicity. With exposure to 0.01 mM 5-FU, 1.25 mM orotate, and 0.0125 mM or less of adenine, however, the relative viability at 120 hours was about the same as with no orotate or adenine, as shown in FIG. 2 (Results E and F). With exposure to 0.01 mM 5-FU and a combination of 2.5 mM orotate and 2.5 mM inosine the relative viability at 120 hours was less than 50% as shown in FIG. 3 (Result I), indicating that the orotate/inosine combination is not able to protect the cells from the 5-FU toxicity. With exposure to 0.01 mM 5-FU, 2.5 mM orotate, 2.5 mM adenine, and uracil in the range of 1.25 mM to 2.5 mM, the relative viability at 120 hours was slightly more than 50% as shown in FIG. 4 (Results J and K), indicating that the presence of uracil counteracts the effect of the orotate/adenine combination, and the cells are not protected from the 5-FU toxicity.

Figure 5:
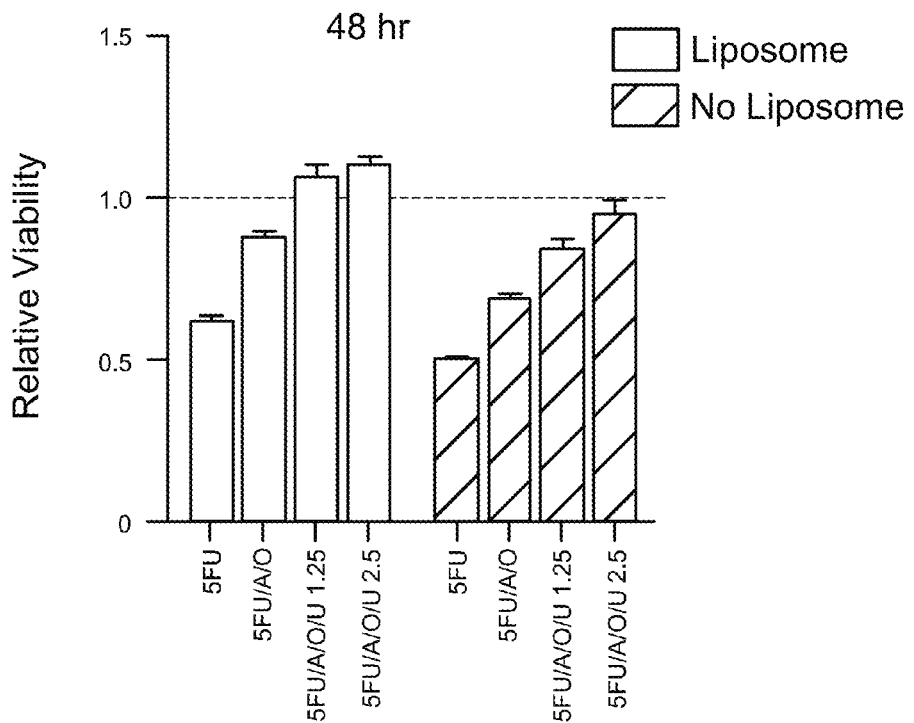
FIG. 5 shows the effect of adenine, orotate, and uracil on the growth of primary human skin cells exposed to 5-FU in cell culture after 48 hours.
Figure 6:
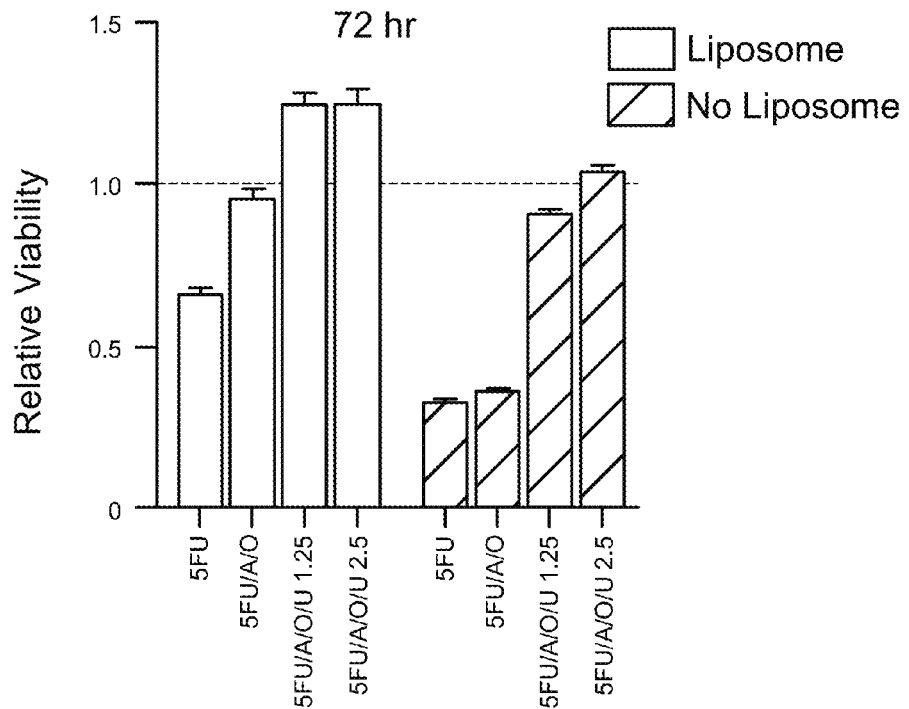
FIG. 6 shows the effect of adenine, orotate, and uracil on the growth of primary human skin cells exposed to 5-FU in cell culture after 72 hours.

FIG. 5 and FIG. 6 show the effect of different combinations of adenine (A), orotate (O), and uracil (U), either in liposomes or without liposomes, in mediating the toxicity to growth of 5-FU for human skin cells in cell culture after incubation at 37° C. The concentration of 5-FU was also 0.01 mM in these trials. The concentration of adenine and orotate, when present, was 2.5 mM. The relative viability of the cells was determined after 48 hours (FIG. 5) or 72 hours (FIG. 6). In contrast to the human-derived colon (Caco-2) cell results, the inclusion of uracil with adenine and orotate actually increases the protection of the human skin cells against 5-FU toxicity, as shown in FIG. 5 and FIG. 6 (Results "5 FU/A/O/U 1.25" and "5 FU/A/O/U 2.5"). Although the adenine/orotate/uracil trials with liposomes produced greater relative cell viabilities than the adenine/orotate/uracil trials without liposomes, it should be noted that the 5-FU control trials with liposomes also produced greater relative cell viabilities than the equivalent trials without liposomes. It appears that liposomes may decrease the efficacy of 5-FU in vitro with unclear implications for the effect of oral liposomes on 5-FU toxicity in vivo.

Orotate is the natural substrate of the enzyme OPT. The activity of the enzyme OPT on 5-FU is decreased by the presence of an excess by saturating the active sites on the enzyme OPT by the natural substrate orotate. The production of toxic metabolite of 5-FU is reduced by the metabolism of 5-FU by the enzyme OPT because the active site of the enzyme OPT is filled with the competing substrate orotate. The competing substrate orotate inhibits 5-FU from entering the active site of the enzyme OPT where it can be further metabolized to the toxic product. Orotate, in comparison to 5-FU, is an acid with a much lower pK and therefore is a much better substrate for OPT.

The competing substrate orotate does not readily enter or exit the cell membrane of the cells lining the mucosa of the intestinal tract, because the substrate orotate has an acidic pK and an overall negative charge, as do the cell membranes of the cells lining the mucosa of the intestinal tract. At an acidic pH condition, the orotate is not charged and is better absorbed into the systemic circulation (see, for example, Robinson et al., "Effects of Orotic Acid Ingestion on Urinary and Blood Parameters in Humans", *Nutrition Research*, Vol. 3, pp. 407-415, 1983).

As mentioned above, 5-FU is also, alternatively, metabolized to its toxic form by the two enzymes UP and TP. Uracil can compete for anabolism with 5-FU via TP and UP. In conditions of excess uracil, the active site on the UP and TP enzymes are filled with uracil thereby decreasing the rate of metabolism of 5-FU by enzymes UP and TP to the toxic form. As noted in FIG. 3, the gland cells (columnar cells) that line the GI tract rely little on the salvage pathways of UP and TP. The result is that the use of uracil increases the toxicity of 5-FU. The likely explanation is that uracil competes well with 5-FU for UP and TP but is not active at all as a substitute for OPT because of its even higher pK than 5-FU (pK of uracil of 9.45>>pK of 5-FU of 7.8).

In contrast, skin cells (squamous), as shown in FIG. 5 and FIG. 6, have the reverse metabolic pathway. That is, TP/UP, in preference to OPT, are formed as squamous cells salvage pyrimidines to grow, as shown in FIG. 5 and FIG. 6. Thus, orotate does not impact skin (squamous) cell response to 5-FU exposure.

This result is intuitively consistent with how squamous cells grow, in layers, with the oldest at the top. As the top (superficial) layer of cells die, their contents are salvaged by the younger cell layer underneath.

Columnar cells absorb nutrition from the GI tract and make de novo pyrimidines. A layered structure would make no sense for nutrient-absorbing columnar cells as would using a strategy of nutrient salvage-dependent growth.

The competing substrate dietary orotate is nontoxic and requires facilitated transport to exit the cell because of its charge at neutral pH. At low pH, as in the stomach, the orotate is not ionized and is absorbed at a higher rate (see, for example, Robinson et al.). Then the orotate/adenine mixture may be given together with a protein pump inhibitor (PPI), such as omeprazole, to retain orotate within the GI tract and reduce systemic exposure to orotate.

It has been observed that cellular exposure to enough orotate, such that the orotate permeates the cell membrane, depletes phosphoribosyl pyrophosphate (PRPP), which is depleted by the enzymatic action of OPT. As de novo purine synthesis also requires consumption of PRPP, the depletion of PRPP by unopposed OPT activity can cause cell death by depleting cellular PRPP pools. This results in decreased purine synthesis and can cause "purine less death". This cellular growth imbalance and tumor formation may be neutralized by the addition of adenine. Adenine is anabolized by phosphoribosyltransferase (APRT) to adenosine monophosphate that is converted by adenosine monophosphate deaminase (AMD) to inosine monophosphate (IMP), a GMP precursor. Thus, "purine less death" is avoided.

The present methods and compositions may have much wider application to treat GI disorders. As can be seen in FIGS. 1, 3, and 4, the exposure of human-derived colon (Caco-2) cells grew better in the presence of a combination of adenine, orotate, and 5-FU than controls without 5-FU. Adenine has in the past been noted to prolong the shelf life of stored blood (see, for example, Bartlett, "Erythrocyte Metabolism", pp. 10-13 in *Adenine and Red Cell Storage, The Human Red Cell in Vitro*, Greenwald et al., ed., New York: Grune and Stratton, 1974).

Adenine, unlike orotate, is uncharged and well-absorbed systemically. Adenine can, however, then be oxidized to 2,8-dihydroxy adenine. 2,8-dihydroxy adenine is poorly soluble and can cause renal stones (see, for example, Van Acker et al., "Complete Deficiency of Adenine Phosphoribosyltransferase", *The New England Journal of Medicine*, Vol. 297, pp. 127-132, 1977). The systemic exposure to adenine must be kept to a minimum.

Adenine also can reverse the systemic toxicity of 5-FU at high doses, which is another reason adenine exposure must be kept to a minimum. FIG. 2 shows that 1.25 mM orotate and 0.125 mM adenine can protect cells from the toxicity of 0.01 mM 5-FU exposure to cell growth, whereas decreasing the concentration of adenine to 0.0125 mM with orotate exposure at 1.25 mM offers no protection from the toxicity of 0.01 mM 5-FU exposure to cell growth.

It has been estimated that systemic exposure (i.e. by intravenous administration) to adenine in a single dose at 20 mg/kg to a human is safe (see, for example, Bartlett). For a 70 kg man, the adenine dosage would be 1.4 g. In the present instance, a 0.125-mM solution of adenine in a liter volume of GI fluid would be a 15 mg total body adenine exposure. Experiments have shown extraction efficiencies in the range of 75% to 85% of adenine introduced in the small intestine in rats (see, for example, Salati et al., "Absorption and Metabolism of Adenine, Adenosine-5'-Monophosphate, Adenosine and Hypoxanthine by the Isolated Vascularly Perfused Rat Small Intestine", *Journal of Nutrition*, Vol. 114, pp. 753-760, 1984). The systemic circulation volume for humans is about 5 liters. Therefore, the systemic exposure to adenine would be well below 1% of 20 mg/kg, which would neither cause renal stones nor rescue 5-FU.

In a preferred embodiment, a slow or controlled release dosage of adenine and orotate is given orally. More preferably, the oral delivery is osmotically-controlled oral drug delivery. A protein pump inhibitor (PPI) is preferably also given concomitantly to cause secretion of neutral gastric juices to prevent orotate absorption in the stomach. Also, allopurinol is preferably administered to decrease conversion of adenine to 2,8-dihydroxy adenine (see, for example, Bührdel et al., "Adenine Therapy in Lesch-Nyhan Syndrome", *Acta Paediatrica Hungarica*, Vol. 26, pp. 327-333, 1985).

In an alternative embodiment, a method and composition promote accumulation of the substrate orotate in the cells lining the mucosa of the intestinal trace by incorporating the substrate orotate with certain substrates of the enzymes into cationic liposomes. Cationic liposomes carry a net positive charge. This net positive charge enables the cationic liposome to be taken up by the negatively charged outer membranes of the cells lining the mucosa of the intestinal tract. By incorporating the substrate orotate and other substrates of enzymes into cationic liposomes, the substrate orotate and the other substrates of enzymes can be delivered to the cells lining the mucosa of the intestinal tract and then be taken up by the individual cells of the intestinal tract. Once taken up by the individual cells of the intestinal tract, the competing substrate orotate can then reduce the activity of the enzyme OPT in metabolizing 5-FU to its toxic by-product by saturating the active site of the enzyme OPT. This saturation of the active site of the enzyme OPT decreases further metabolism of 5-FU by the enzyme OPT. The cells lining the mucosa of the intestinal tract are thus relatively protected from the toxic, active 5-FU metabolites. The purine/pyrimidine substrates included in the cationic liposome further decrease the metabolism of 5-FU. The cationic liposomes, because of their charge, minimally permeate the body and release the substrate orotate to alter 5-FU metabolism in the cancerous tumor.

Many cationic lipids have been developed and used in cationic liposome preparation. While the cationic lipids have many different chemical structures, cationic lipids are all composed of a cationic head group composed of primary, secondary, tertiary, or quaternary amines. The primary, secondary, tertiary, or quaternary amines are attached to a hydrophobic group via a linker.

When placed in an aqueous solution, the cationic lipids form liposomes in which the cationic head is on the outside surface of the liposome and the hydrophobic group is on the inside of the liposome. By use of this process a three dimensional bag or sack is formed. The three-dimensional bag or sack contains the substrate orotate and other substrates of enzymes within the interior of the cationic liposome. Since the cationic head of the lipid is located on the surface of the cationic liposome, the positive charge associated with the cationic lipid is located on the outside surface of the cationic liposome.

Some of the commercially available cationic lipids and their suppliers are listed below:

Lipofect ACE (Life Technologies)
Lipofection (Life Technologies)
LipofectAmine (Life Technologies)
CeliFectin (Life Technologies)
DMRIE-C (Life Technologies)
DDAB (Sigma)
DC-Chol (Sigma)
DOTAP (Boehringer Mannheim, Avanti Polar Lipids, Biontex)
MRX-230 and MRX-220 (Avanti Polar Lipids)
Transfectam (Promega)
Transfast (Promega)
Tfx 10, Tfx 20, and Tfx 50 (Promega)
Prefection-CaPO$_4$ (Promega)
Prefection-DEAE-Dextran (Promega)
GeneSHUTTLE-40 (Quantum Biotechnologies)
CLONfectin (Clontech)
METAFECTENE (Biontex)
INSECTOGENE (Biontex)
Effectene (Qiagen)
FuGENE 6 (Roche Molecular Biochemicals)
GENESEAL (MTTI)

In preparing the cationic liposome, a cationic lipid or a combination of cationic lipids are dissolved in an organic solvent such as chloroform or methanol. The solvent is then removed by use of a vacuum or by blowing an inert gas over the solution followed by rehydration in an aqueous solution. The aqueous solution used for rehydration contains the substrate orotate and other substrates of enzymes which metabolize the cancer treatment drug. As the cationic liposome forms due to hydrophobicity of the cationic lipids, the aqueous solution containing the substrate orotate and other substrates of enzymes which metabolize the cancer treatment drug are trapped within the interior of the cationic liposome. The cationic liposomes containing the substrate orotate and other substrates of enzymes which metabolize the cancer treatment drug are then made to a uniform size by either sonication or membrane extrusion.

The cationic liposome is a targeted vector to gastro-intestinal mucosa and does not provide a systemic source of nucleotide precursors.

Those of ordinary skill in the art will understand that in some embodiments, liposomes are used to deliver a purine or pyrimidine substrate to the cells lining the mucosa of the intestinal tract without raising the systemic levels of the delivered material. The reason for not raising the systemic levels of the delivered material is that a substance such as the substrate orotate may salvage a tumor from the effects of the 5-FU chemotherapy. Liposomes have never been used to accomplish this function. Rather, liposomes are typically used to cause a substance to enter a cancerous tumor or to enter into an organ such as the liver. Herein, a substance like the substrate orotate is used only to get into the cells lining the mucosa of the intestinal tract. Such function then becomes an asymmetric drug delivery system and method wherein different amounts of a drug are delivered to different parts of the body.

All above-mentioned references are hereby incorporated by reference herein.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

I claim:

1. A method for prevention of gastrointestinal toxicity in a plurality of gastrointestinal cells caused by administration of 5-fluorouracil to a cancer patient, the method comprising the steps of:
    a) administering the 5-fluorouracil to the cancer patient at a treatment dosage sufficient to cause a cancer cell toxicity of cancer cells of the cancer patient; and
    b) administering adenine and orotate to the cancer patient at a sustained dosage sufficient to prevent gastrointestinal toxicity in the plurality of gastrointestinal cells from the 5-fluorouracil administered in step a) but insufficient to give systemic levels of adenine and orotate to salvage the cancer cells from the cancer cell toxicity of the 5-fluorouracil administered in step a), wherein the sustained dosage provides the adenine at a concentration of at least 0.125 mM to the plurality of gastrointestinal cells of the patient and wherein gastrointestinal toxicity is prevented.

2. The method of claim 1, wherein the adenine and orotate are orally administered to the cancer patient.

3. The method of claim 2, wherein the adenine and orotate is administered in an osmotically-controlled oral drug delivery device.

4. The method of claim 2, wherein the adenine and orotate is administered in cationic liposomes.

5. The method of claim 2 further comprising administering allopurinol to the cancer patient.

6. The method of claim 2 further comprising administering omeprazole to the cancer patient.

7. The method of claim 2, wherein the sustained dosage provides the adenine at a concentration of at least 0.62 mM to the plurality of gastrointestinal cells of the patient.

8. The method of claim 2, wherein the sustained dosage provides the adenine at a concentration of at least 1.25 mM to the plurality of gastrointestinal cells of the patient.

9. The method of claim 2, wherein the sustained dosage provides the adenine at a concentration in a range of 0.125 mM to 2.5 mM to the plurality of gastrointestinal cells of the patient.

10. The method of claim 2, wherein the sustained dosage provides the orotate at a concentration in a range of 1.25 mM to 2.5 mM to the plurality of gastrointestinal cells of the patient.

11. The method of claim 2, wherein the sustained dosage provides the adenine at a concentration in a range of 0.125 mM to 2.5 mM and the orotate at a concentration in a range of 1.25 mM to 2.5 mM to the plurality of gastrointestinal cells of the patient.

12. The method of claim 2, wherein the treatment dosage exposes the plurality of gastrointestinal cells of the patient to a concentration of the 5-fluorouracil of 0.01 mM.

13. The method of claim 2, wherein the sustained dosage is sustained for 120 hours.

14. The method of claim 2, wherein the plurality of gastrointestinal cells comprises substantially all gastrointestinal cells of the patient such that the method prevents gastrointestinal toxicity in substantially all gastrointestinal cells of the patient.

15. The method of claim 1, wherein the adenine and orotate is administered in cationic liposomes.

16. The method of claim 1 further comprising administering allopurinol to the cancer patient.

17. The method of claim 1 further comprising administering omeprazole to the cancer patient.

18. The method of claim 1, wherein the sustained dosage provides the adenine at a concentration of at least 0.62 mM to the plurality of gastrointestinal cells of the patient.

19. The method of claim 1, wherein the sustained dosage provides the adenine at a concentration of at least 1.25 mM to the plurality of gastrointestinal cells of the patient.

20. The method of claim 1, wherein the sustained dosage provides the adenine at a concentration in a range of 0.125 mM to 2.5 mM to the plurality of gastrointestinal cells of the patient.

21. The method of claim 1, wherein the sustained dosage provides the orotate at a concentration in a range of 1.25 mM to 2.5 mM to the plurality of gastrointestinal cells of the patient.

22. The method of claim 1, wherein the sustained dosage provides the adenine at a concentration in a range of 0.125 mM to 2.5 mM and the orotate at a concentration in a range of 1.25 mM to 2.5 mM to the plurality of gastrointestinal cells of the patient.

23. The method of claim 1, wherein the treatment dosage exposes the plurality of gastrointestinal cells of the patient to a concentration of the 5-fluorouracil of 0.01 mM.

24. The method of claim 1, wherein the sustained dosage is sustained for 120 hours.

25. The method of claim 1, wherein the plurality of gastrointestinal cells comprises substantially all gastrointestinal cells of the patient such that the method prevents gastrointestinal toxicity in substantially all gastrointestinal cells of the patient.

* * * * *